US008815232B2

(12) United States Patent
Tepic et al.

(10) Patent No.: US 8,815,232 B2
(45) Date of Patent: Aug. 26, 2014

(54) COMPOSITIONS AND METHODS FOR TREATING CANCER (75) Inventors: Slobodan Tepic, Zurich (CH); Goran Cvetkovic, Zurich (CH)

(73) Assignee: Kyon Biotech AG, Zurich (CH)

( * ) Notice: Subject to any disclaimer, the term of this patent is extended or adjusted under 35 U.S.C. 154(b) by 0 days.

(21) Appl. No.: 13/060,790

(22) PCT Filed: Aug. 25, 2009

(86) PCT No.: PCT/EP2009/060906
§ 371 (c)(1),
(2), (4) Date: Aug. 16, 2011

(87) PCT Pub. No.: WO2010/023195
PCT Pub. Date: Mar. 4, 2010

(65) Prior Publication Data
US 2011/0300109 A1    Dec. 8, 2011

Related U.S. Application Data (60) Provisional application No. 61/091,996, filed on Aug. 26, 2008.

(51) Int. Cl.
*A61K 38/43* (2006.01)
*A61K 38/46* (2006.01)

(52) U.S. Cl.
CPC ............. *A61K 38/46* (2013.01); *A61K 2300/00* (2013.01)
USPC ........................................................ 424/94.1

(58) Field of Classification Search
None
See application file for complete search history.

(56) References Cited

U.S. PATENT DOCUMENTS

| | | | |
|---|---|---|---|
| 4,955,857 A | 9/1990 | Shettigar | |
| 5,372,942 A | 12/1994 | McGarrity et al. | |
| 5,626,862 A * | 5/1997 | Brem et al. | 424/426 |
| 6,165,975 A | 12/2000 | Adams et al. | |
| 6,251,388 B1 | 6/2001 | Durden | |
| 6,261,557 B1 | 7/2001 | Tepic et al. | |
| 6,737,259 B1 | 5/2004 | Clark | |
| 2001/0041191 A1 | 11/2001 | Valletta | |
| 2003/0017146 A1* | 1/2003 | Tepic et al. | 424/94.6 |
| 2004/0057926 A1 | 3/2004 | Ochoa et al. | |
| 2005/0215959 A1* | 9/2005 | Whitington | 604/270 |
| 2005/0244398 A1* | 11/2005 | Cheng et al. | 424/94.4 |

FOREIGN PATENT DOCUMENTS

| | | |
|---|---|---|
| EP | 1859810 A1 | 11/2007 |
| EP | 1031352 A2 | 8/2008 |
| WO | WO9300807 | 1/1993 |
| WO | WO93/01824 | 2/1993 |
| WO | WO9404193 | 3/1994 |
| WO | WO9806421 A1 | 2/1998 |
| WO | WO02074835 | 9/2002 |
| WO | WO03063780 A2 | 8/2003 |
| WO | WO 03063780 A2 * | 8/2003 |
| WO | WO2004000349 A1 | 12/2003 |
| WO | WO2005/077405 | 8/2005 |
| WO | WO2006114691 | 11/2006 |

OTHER PUBLICATIONS

Ascierto et al. "Pegylated Arginine Deiminase Treatment of Patients with Metastatic Melanoma: Results from Phase I and II Studies." (2005) Journal of Clinical Oncology, vol. 23, 7660-7667.*
Wheatley et al. "Arginine Catabolism, Liver Extracts and Cancer" (2002) Pathology Oncology Research, vol. 8, 18-25.*
Wu, "Intestinal Mucosal Amino Acid Catabolism." (1998), Journal of Nutrition, vol. 128, 1249-1252.*
Bender et al., "Malignant Melanoma: Pattern of Metastasis to the Small Bowel, Reliability of Imaging Studies, and Clinical Relevance." (2001) Journal of Gastroenterology, vol. 96, 2392-2400.*
Morris, "Arginine: beyond protein." (2006) American Journal of Clinical Nutrition, vol. 83, 508S-512S.*
Lind, "Arginine Metabolism: Enzymology, Nutrition, and Clinical Significance." (2004) The Journal of Nutrition: Symposium on Arginine: 2837S-2841S.*
Cheng et al. "Remission of hepatocellular carcinoma with arginine depletion induced by systemic release of endogenous hepatic arginase due to transhepatic arterial embolisation, augmented by high-dose insulin: arginase as a potential drug candidate for hepatocellular carcinoma." (2005) Cancer Letters, vol. 224: 67-80.*
Alonso and Rubio, "Participation of Ornithine Aminotransferase in the Synthesis and Catabolism of Ornithine in Mice," Biochem. J. 259:131-138, 1989.
Ameen et al., "Inhibition of Urea Cycle Enzymes by Lysine and Saccharopine," Biochem. Int. 14(3)395-400, 1987.
Ascierto et al., "Pegylated Arginine Deiminase Treatment of Patients with Metastatic Melanoma: Results from Phase I and II Studies," J. Clin. Oncol. 23(30):7660-7668, 2005.
Bender et al., "Malignant Melanoma: Patterns of Metastasis to the Small Bowel, Reliability of Imaging Studies, and Clinical Relevance," Am. J. Gastroenterol. 96(8):2392-2400, 2001.

(Continued)

*Primary Examiner* — Jon P Weber
*Assistant Examiner* — Teresa E Knight
(74) *Attorney, Agent, or Firm* — Occhiuti & Rohlicek LLP (57) ABSTRACT

The present invention is based, in part, on our discovery of compositions and methods that can be used to systemically deplete arginine and thereby treat arginine-dependent cancers. Our studies indicate that administering a composition that depletes arginine directly to the patient's small intestine will provide effective treatment for arginine-dependent cancers. Moreover, the methods can be carried out in such a way that various sources of arginine are restricted and side effects are minimized. For example, to deplete arginine, one can not only administer an arginine-depleting enzyme directly to the intestinal lumen but can also inhibit endogenous production of arginine, reduce arginine production by intestinal bacteria and limit arginine intake. To minimize side effects, one can inhibit protein breakdown, which may occur as a compensatory mechanism, provide systemic NO from a nitric oxide donor, provide a pressor peptide, and/or provide prostacycline or an analog thereof.

15 Claims, 6 Drawing Sheets

(56) References Cited

OTHER PUBLICATIONS

Broome, "Evidence that the L-Asparaginase Activity of Guinea Pig Serum is Responsible for its Antilymphoma Effects," Nature 191:1114,-1115 1961.

Burns et al. "Arginine: An Indespensable Amino Acid for Mature Dogs," J. Nutr. 111:1020-1024, 1981.

Campbell et al., "Two L-Asparaginases from *Escherichia coli* B. Their Separation, Purification, and Antitumor Activity," Biochem. 6:721-730, 1967.

Csáky and Fekete, "Soybean: Feed Quality and Safety Part 1: Biologically Active Components A Review," Acta Veterinaria Hungarica 52(3):299-313, 2004.

Curley et al., "Regression of Hepatocellular Cancer in a Patient Treated with Arginine Deiminase," Hepato-Gastroenterol. 50:1214-1216, 2003.

Douglas et al., "The Effects of Infusion of Insulinlike Growth Factor (IGF) I, IGF-II, and Insulin on Glucose and Protein Metabolism in Fasted Lambs," J. Clin. Invest. 88:614-622, 1991.

Furth-Walker et al., "Relationship Between Blood, Liver and Brain Pyridoxal Phosphate and Pyridoxamine Phosphate Concentrations in Mice," J. Nutr. 120(11):1338-1343, 1990.

Green et al., "The Purification and Characterization of Arginase from *Saccharomyces cerevisiae*," J. Biol. Chem. 265 (3):1601-1607, 1990.

Herndon et al., "Muscle Protein Catabolism After Severe Burn: Effects of IGF-1/IGFBP-3 Treatment", Annals of Surgery 229(5):713-722, 1999.

Howard and Carpenter, "L-Asparaginase from *Erwinia carotovora*," J. Biol. Chem. 247:1020-1030, 1972.

Ikemoto et al., "Expression of Human Liver Arginase in *Escherichia coli*," Biochem. J. 270(3):697-703, 1990.

Morris, "Arginine: Beyond Protein," Am. J. Clin. Nutr. 83(suppl):508S-512S, 2006.

Ohno and Hersh, "Immunosuppressive Effects of I-Asparaginase," Cancer Res. 30:1605-1611, 1970.

Ortega et al., "I-Asparaginase, Vincristine, and Prednisone for Induction of First Remission in Acute Lymphocytic Leukemia," Cancer Res. 37:535-540, 1977.

Patchett et al., "Characterisation of arginase from the extreme thermophile '*Bacillus* caldovelox'," Biochim. Biophys. Acta 1077(3):291-298, 1991.

Rogers, "Significance of Dialysis against Enzymes to the Specific Therapy of Cancer and Genetic Deficiency Diseases," Nature 220:1321-1322, 1968.

Scott et al., "Single Amino Acid (Arginine) Deprivation: Rapid and Selective Death of Cultured Transformed and Malignant Cells," Br. J. Cancer 83:800-810, 2000.

van Den Hout et al., "Inactivation Kinetics Study of the Kunitz Soybean Trypsin Inhibitor and the Bowman-Birk Inhibitor," J. Agric. Food Chem. 46(1):281-285, 1998.

Wan et al., "Urinary Excretion of Bowman-Birk Inhibitor in Humans After Soy Consumption as Determined by a Monoclonal Antibody-based Immunoassay," Cancer Epidemiol. Biomarkers Prev. 9(7):741-747, 2000.

Wheatley and Campbell, "Arginine Catabolism, Liver Extracts, and Cancer," Pathol. Oncol. Res. 8(1):18-25, 2002.

Wheatley, "Controlling Cancer by Restricting Arginine Availability—Arginine-catabolizing Enzymes as Anticancer Agents," Anticancer Drugs 15:825-833, 2004.

Wu et al., "Endogenous Synthesis of Arginine Plays an Important Role in Maintaining Arginine Homeostasis in Postweaning Growing Pigs," *J. Nutr.* 127(12):2342-2349, 1997.

Wu et al., "Synthesis of citrulline and arginine from proline in enterocytes of postnatal pigs," Am. J. Physiol. Gastrointest. Liver Physiol. 272(6 Pt 1):G1382-G1390, 1997.

Wu, "Intestinal Mucosal Amino Acid Catabolism," J. Nutr. 128:1249-1252, 1998.

* cited by examiner

COMPOSITIONS AND METHODS FOR TREATING CANCER

CROSS-REFERENCE TO RELATED APPLICATIONS

This application is a U.S. national phase application filed under 35 U.S.C.§371 of International Application No. PCT/EP2009/060906, filed Aug. 25, 2009, which claims the benefit of the filing date of U.S. Provisional Application No. 60/091,996, filed Aug. 26, 2008. The contents of the earlier-filed applications are hereby incorporated by reference in their entireties.

TECHNICAL FIELD

This invention relates to methods for treating cancer and more particularly to methods in which an arginine-depleting enzyme is administered directly to the lumen of a patient's small intestine.

BACKGROUND

Methods of treating cancer by limiting the supply of an amino acid have been suggested previously. For example, asparaginase was found to be the active agent in guinea pig serum that inhibited the growth of certain asparagine-dependent mammalian tumors (see Broome, *Nature* 191:1114, 1961). Microbial asparaginase isolated from *E. coli* and *E. carotovora* were also shown to act as potent anti-leukemic agents (see Howard and Carpenter, *J. Biol. Chem.* 247:1020, 1972 and Campbell et al., *Biochem.* 6:721, 1967). When one of these enzymes was utilized in combination with the chemotherapeutic agent vincristine and the corticosteroid prednisone for the treatment of acute lymphoblastic or acute undifferentiated human leukemia, an overall remission rate of 93% was reported (Ortega et al., *Cancer Res.* 37:535, 1977). Microbial asparaginases resulted in a wide range of host toxicity, however, including hepatic, renal, splenic, and pancreatic dysfunction (Ohno and Hersh, *Cancer Res.* 30:1605, 1970; see also U.S. Pat. No. 6,251,388).

Another amino acid, arginine, has also been manipulated for cancer treatment. Arginine is considered a semi-essential amino acid because the body can produce some, but usually not all, of the arginine that it requires through a synthetic pathway that utilizes the non-essential amino acids proline and glutamine (or glutamate) as precursors. Newborn mammals are particularly dependent on endogenous production of arginine via the intestinal-renal axis, whereby citrulline is produced in the small intestine and then converted to arginine in the kidneys.

In vitro experiments have shown that a number of cancer cell lines cannot survive more than a few days when arginine is depleted to the micromolar range (Scott et al. Br. *J. Cancer* 83:800-810, 2000; and for review, Wheatley, *Anticancer Drugs* 15:825-833, 2004). It is difficult to attain this level of depletion in vivo, however. The prevailing approach has been systemic administration of an arginine-degrading enzyme, which can remove arginine released into the circulation from any one of the potential sources of this amino acid (Tepic and Pyk, U.S. Pat. No. 6,261,557; Clark, U.S. Pat. No. 6,737,259; and Wheatley and Campbell, *Pathol. Oncol. Res.*, 8:18-25, 2002).

In addition to arginases, arginine is also a substrate for nitric oxide synthase (NOS), which converts arginine into citrulline and nitric oxide (NO). There are several types of NOS, reflecting the wide-ranging and very important roles of NO. Arginine is also a substrate for arginine decarboxylase (ADC), which converts arginine to agmatine (and $CO_2$). ADC is present in the brain and kidneys of mammals, but the metabolic role of agmatine remains rather poorly understood. Three additional enzymes that utilize arginine as a substrate are known: arginine kinase, arginine 2-monooxigenase and glycine amidinotransferase.

SUMMARY

The present invention is based, in part, on our discovery of compositions and methods that can be used to systemically deplete arginine and thereby treat arginine-dependent cancers. Our studies indicate that administering a composition that depletes arginine directly to the patient's small intestine will provide effective treatment for arginine-dependent cancers. Moreover, the methods can be carried out in such a way that various sources of arginine are restricted and side effects are minimized. For example, to deplete arginine, one can not only administer an arginine-depleting enzyme directly to the intestinal lumen but can also inhibit endogenous production of arginine, reduce arginine production by intestinal bacteria and limit arginine intake. To minimize side effects, one can inhibit protein breakdown, which may occur as a compensatory mechanism, provide systemic NO from a nitric oxide donor, provide a pressor peptide, and/or provide prostacycline or an analog thereof.

The present compositions and methods can achieve not only arginine depletion but also depletion of ornithine and citrulline. Arginine is normally transported from the gut lumen into circulation, but the flux can be reversed if the concentration of arginine in the gut is very low. The exchange happens over the large surface area between the lumen of the small intestine and the vascular and lymphatic circulatory systems. In the present methods, back-transport of the conversion product, ornithine, is surprisingly blocked, limiting the availability of ornithine for conversion to citrulline in the intestine and then to arginine in the kidneys. The result is a substantial systemic reduction of arginine, ornithine and citrulline. Depletion of these three amino acids can be facilitated by restricting essentially all sources of arginine and effecting its enzymatic conversion to ornithine within the lumen of the gut.

Practically, direct administration can be achieved by delivering the arginine-depleting enzyme to the small intestine by a nasointestinal feeding tube or a feeding tube inserted through a jejunostomy, esophagostomy, or gastrostomy. The amount and duration of the treatment, in any of the forms described herein, can be such that the plasma concentration of arginine is reduced to about 1 to 10 micromolar (e.g., below about 5 micromolar (5 µM)).

The present compositions can be administered for a limited time (i.e., treatment can be acute), and may be repeated after periods of rest. For example, treatment sessions can last for about two days and up to about one week (i.e., about 1, 2, 3, 4, 5, 6, 7 or 8 days).

As noted, in addition to direct administration of an arginine-depleting enzyme to the lumen of the small intestine, the treatment regime can include aggressive reduction in nutritional intake of arginine and/or inhibition of the breakdown of body protein. For example, one can inhibit protein breakdown by stimulating endogenous production of insulin through consumption of carbohydrates and/or by pharmacological intervention with insulin, insulin-glucose clamp, or an insulin like growth factor (IGF-I). Insulin is a potent growth hormone produced by pancreas. It stimulates protein synthesis, inhibits protein breakdown, promotes glucose and lipid uptake by cells, and is used as a drug for treating diabetes. Insulin-like growth factors I and II (IGF-I and IGF-II) are potent growth hormones produced by the liver upon stimulation with growth hormone. They stimulate protein synthesis and inhibit protein breakdown but have little effect on glucose. An insulin-glucose clamp is a state induced by a therapeutic composition, most frequently used to assess insulin resistance.

Where exogenous sources of arginine are restricted, one can administer an amino acid mixture that lacks arginine, ornithine, and citrulline but contains one or a combination of: leucine, isoleucine, histidine, phenylalanine, tryptophan, threonine, valine, lysine and methionine. Other ways in which the patient's diet may be modulated during the period of arginine depletion include the administration or consumption of a hydrolysate of casein, a carbohydrate (e.g., glucose), a slow metabolizing carbohydrate (e.g., a starch) and/or a non-metabolizing substance such as cellulose or inulin. In any embodiment, the patient may also receive physiological electrolytes.

Alternatively or in addition, one can administer an agent to reduce or eliminate production of arginine by intestinal bacteria. For example, one can sterilize the gut with suitable antibiotics (e.g., gentamicin, vancomycin, teicoplanin, neomycin, netilmicin, or amikacin). Vancomycin is a glycopeptide antibiotic used in the prophylaxis and treatment of infections caused by Gram-positive bacteria. It is not absorbed through the gut and is indicated for gut sterilization in combination with, for example, gentamicin. Gentamicin is an aminoglycoside antibiotic that is active against many types of bacteria, particularly Gram-negative bacteria.

As even a transient state of arginine depletion can lead to unwanted side effects (e.g., perturbation of blood clotting mechanisms and hemodynamics), an NO donor (e.g., sodium nitroprusside, nitroglycerine or isosorbide dinitrate (ISDN)) and/or a vasoconstricting or "pressor" peptide (e.g., vasopressin, ornipressin, desmopressin, or terlipressin) can be administered during the session of arginine depletion. Nitric oxide donors release NO, either directly or via metabolic conversions of certain substrates. Sodium nitroprusside (SNP), which is approved for the treatment of hypertension, decomposes to NO and cyanide and is therefore a direct NO donor. Nitroglycerine, in contrast, is an indirect NO donor (currently approved for treatment of angina pectoris). ISDN is also an indirect NO donor. Terlipressin is an analog of vasopressin, which is a posterior pituitary hormone that acts as an anti-diuretic. Ornipressin is also an analog of vasopressin in which ornithine is substituted for arginine. One can further include or administer prostacycline, a prostaglandin I2 that inhibits platelet aggregation, or an analog thereof (e.g., iloprost).

Use of hydroxocobalamin (B12a, or precursor to vitamin B12) as an antidote for cyanide (which is a byproduct of SNP decomposition) is recommended at a double molar rate to that of SNP. Alternatively, sodium thiosulfate, which is also an antidote for cyanide can be used at 5 to 10 times the molar rate of SNP.

As most cancers will respond to restriction of arginine, ornithine, and citrulline, the present compositions and methods are widely applicable. More specifically, the present compositions can be used to treat cancers of the blood, liver, breast, bone, lung, pancreas, skin, reproductive system, brain, soft connective tissue, or gastrointestinal tract.

In addition to the direct effect on arginine-dependent tumors, we believe arginine restriction can also serve as a protective measure for healthy, dividing cells, including those of the intestinal lining and bone marrow, which will respond by exiting into a rest phase of the cell cycle. Thus, the present compositions and methods can also serve as adjunct therapeutics and therapies, respectively, and can allow deployment of more extreme chemotherapy and/or radiation therapy. After a period of time (e.g., a few hours to about three days), chemotherapeutic agents can be dialyzed out of circulation before restoring arginine, ornithine and citrulline to about their pre-treatment levels and allowing healthy cells to resume proliferation. Accordingly, any of the methods described herein can be carried out alone or together with surgically ablating a tumor within the patient, subjecting the patient to radiation treatment for the cancer, or administering a chemotherapeutic agent in addition to an arginine-depleting enzyme to the patient.

In accordance with the description above, the present invention features methods of treating a patient who has cancer by, inter alia, administering an arginine-depleting enzyme, or a biologically active variant thereof, directly to the lumen of the patient's small intestine. These methods can be carried out before, during, or after a patient has received another type of cancer treatment (e.g., surgery, a conventional chemotherapeutic agent or a radiation treatment), and any of these methods can also include the step of identifying a patient in need of treatment prior to performing surgery, the chemotherapy, radiation therapy and/or arginine-depleting therapy. Where arginine-depleting therapy is carried out in conjunction with chemotherapy, one may be able to deliver the chemotherapeutic at much higher doses than would otherwise be possible. While the methods are not limited to those in which any particular cellular mechanism is at work, it is our expectation that arginine depletion allows more aggressive chemotherapy for the reason stated above; healthy, normally proliferating cells are protected by exit to the resting phase of the cell cycle in response to arginine depletion.

The present compositions can include an arginine-depleting enzyme or a biologically active variant thereof. More generally, any of the protein-based agents suitable for inclusion in the present compositions or suitable for administration in the present methods can be biologically active variants of naturally occurring proteins. For example, wherever an enzyme (e.g., arginase or ADC) or growth factor (e.g., IGF-I) is effectively administered, one can administer a biologically active variant thereof. Biologically active variants include proteins that exhibit a certain extent of similarity or identity to the corresponding wild type sequence and retain sufficient biological activity to be useful in the present methods. For example, a biologically active variant of a protein (e.g., an arginine-depleting enzyme) may be at least or about 80%, 85%, 90%, 95%, 96%, 97%, 98% or 99% homologous to or identical to the corresponding wild type enzyme and can retain at least or about 50%, 60%, 70%, 75%, 80%, 85%, 90%, 95% or more of the efficacy of the cognate wild type protein in a cell death assay (e.g., a cell death study in tissue culture or an in vivo setting).

Many sources of arginine-depleting enzymes can be used as well. The enzymes that can be included in the present compositions and delivered by the present methods include virtually any enzyme that depletes or degrades arginine. For example, the arginine-depleting enzyme can be an arginine-depleting enzyme naturally expressed by an animal cell (e.g., a human cell, such as a human liver cell, or a cell of a pig, cow, ox, horse or sheep), a bacterial cell, or a yeast cell (e.g., *S. cerevisciae*).

Further, and regardless of the initial source, the arginine-depleting enzyme can be an arginase (e.g., Type I arginase); an arginine decarboxylase; an arginine deiminase (which converts L-arginine and water to L-citrulline and ammonia); an arginine kinase (which converts L-arginine and ATP to N^ω-phosphor-arginine and ADP); an arginine 2 monooxigenase (which converts L-arginine and oxygen to 4-guanidinobutanamide, carbon dioxide and water); or a glycine amidinotransferase (which converts L-arginine and glycine to L-ornithine and guanidinoacetate). The enzymes can be used alone or in combination, and can be administered by way of intact cells, homogenates, or lysates. The enzymes can also be recombinantly produced and may be, but are not necessarily, purified to varying extents. For example, one can administer a liver homogenate or a partially purified liver cell extract.

In some preparations, the tissue (e.g., liver) will also include lactate at concentrations high enough to inhibit intestinal production of citrulline (via ornithine) from proline. This is an early step in the so-called intestinal-renal axis, a major endogenous source of arginine. In the body, lactic acid is ionized to lactate (L-lactate). It is constantly produced in muscles during normal metabolism and exercise and is removed by oxidation to pyruvate by well-oxygenated muscle cells.

Prepared liver tissue (e.g., a homogenate or extract) can also contain pyridoxal phosphate. Pyridoxal phosphate is a co-factor for many enzymes; the active form of vitamin B6, which comprises three natural organic compounds: pyridoxal, pyridoxamine and pyridoxine. The concentration of pyridoxal phosphate is not, however, usually high enough to cause sufficient inhibition of the second pathway of citrulline production in the intestine from glutamate. Therefore, liver preparations may be supplemented with pyridoxal phosphate, and any of these compositions (e.g., liver extracts containing an arginine-depleting enzyme with or without additional lactate and/or pyridoxal phosphate) are within the scope of the present invention.

Other useful inhibitors of arginine production through the intestinal-renal axis are Gly-Gly-PALO and gabaculine. Gly-Gly-PALO is a glycylglycine derivative of delta-N-(phosphonacetyl)-L-ornithine (PALO), a powerful and specific inhibitor of carbamoyltransferase, which converts ornithine to citrulline. Gly-Gly-PALO has been shown to cross into intestinal lining cells, whereas PALO does not.

Any of the present compositions can include a liver extract in crude form, partially purified, concentrated by the removal of liquid and/or sterilized as well as pharmaceutically acceptable carriers in which the present active agents (e.g., arginase and/or lactate and/or pyridoxal phosphate) are included. Thus, the present compositions include those that are not suitable for administration by other routes of administration (e.g., intravenous, intramuscular, or subcutaneous).

The arginine-depleting enzyme can be administered at a rate equal to or higher than about 200 units per kilogram per day. In certain instances up to 20000 units could be administered per kilogram per day. As used herein, one unit of an arginine-depleting enzyme is an amount of the enzyme that converts one micromole of arginine to urea per minute.

Just as the arginine-depleting enzyme can be administered in a tissue preparation such as liver, it can be administered in non-animal cells, such as intact or lysed bacterial cells (e.g., a species of *Bacillus* such as *Bacillus caldovelox*) or yeast cells (e.g., a strain of *Saccharomyces cerevisiae*, more commonly known as baker's yeast).

In any instance where an arginine-depleting enzyme is formulated or administered, it may be formulated with or administered with an essential co-factor of the arginine-depleting enzyme. For example, the arginine-depleting enzyme can be an arginase and the essential co-factor can be manganese. The various compositions and methods can further include an ornithine-depleting enzyme (e.g., ornithine decarboxylase) and, optionally, an ornithine decarboxylase co-factor (e.g., pyridoxal phosphate).

Agents that can be included in the present compositions and/or administered separately include agents that inhibit protein breakdown in the patient, such as insulin, an insulin-like growth factor, or a growth hormone. One can further include or administer glucose, dextrose, or fructose to the patient. The components of the present compositions can be physically combined (e.g., mixed) or combined by virtue of inclusion within separate containers within a kit. The kit can further include instructions (e.g., printed or recorded instructions) for use.

The present methods have been characterized as methods of treatment. The present compositions can, however, also be characterized in terms of their use. Accordingly, the present invention encompasses use of any of the compositions described herein in the preparation of a medicament (e.g., in the preparation of a medicament for treatment of an arginine-dependent cancer).

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2 is a diagram illustrating a synthetic pathway by which glutamine is converted to ornithine, citrulline, and then arginine. Proline is also an important precursor for citrulline synthesis in the cells lining the intestine (see Wu, *Am. J. Physiol.* 272(6 Pt 1):G1382-G1390, 1997). The enzymes of the intestinal-renal axis, as marked on FIG. 2, are: phosphate-dependent glutaminase (1); $\Delta^1$-L-pyrroline-5-carboxylate (P5C) synthase (a bifunctional enzyme) (2); glutamate aminotransferase (3); P5C synthase (a bifunctional enzyme) (4); spontaneous chemical reaction (5); ornithine aminotransferase (6); proline oxidase (7); ornithine carbamoyltransferase (8); carbamoylphosphate synthase (9); argininosuccinate synthase (10); and argininosuccinate lyase (11).

FIG. 9 is a line graph showing loss of platelets in experimental dogs subjected to arginine depletion. The dogs in Group A (11 shown here) did not receive any NO donor; the dog B was on full-intensity dialysis, the most extreme treatment, yet he showed only a modest platelet loss during a five-day session. An NO donor, sodium nitroprusside (SNP) and prostacycline were continuously infused, together with vasopressin to offset the effect of NO on vascular tonus.

DETAILED DESCRIPTION

We have discovered that administering an arginine-depleting enzyme directly to the lumen of the small intestine results in systemic depletion of arginine. While arginine remains effectively transported into the lumen from the vasculature and lymphatic circulation, the ornithine into which it is converted cannot, surprisingly, move back into circulation or the lining cells of the small intestine. As a result, ornithine is not available as a precursor for citrulline production in the lining cells of the small intestine and, consequently, citrulline is not available for conversion to arginine in the kidneys. The large surface of the intestinal endothelium therefore becomes an effective trap for systemic arginine. Use of arginine by the body and its enzymatic degradation within the intestinal lumen can reduce the amount of free arginine from extracellular pools down to the micromolar range. At that level, cancer cells cannot survive. Accordingly, described herein are, inter alia, methods and compositions for treating arginine-dependent cancers.

Arginine-depleting Enzymes: The enzymes that can be included in the present compositions and delivered by the present methods include virtually any enzyme that depletes or degrades arginine. Exemplary arginine-depleting enzymes include, but are not limited to, an arginase (e.g., a Type I arginase). Arginases convert L-arginine and water to L-ornithine and urea. Arginase Type I is found at high concentrations in many tissues including the liver and erythrocytes, and other isoforms are widely distributed in basically all tissues of all animals. Arginases are also present in plants, yeast, and bacteria, and any of these sources are suitable sources for the present compositions and methods. Other arginine-depleting enzymes include arginine decarboxylases, arginine deiminases, arginine kinases, arginine 2 monooxygenases, and glycine amidinotransferases. Any of these enzymes, as expressed by human, animal, bacterial, and yeast cells can be used in the compositions and methods described herein.

The arginine-depleting enzyme can be a full-length, naturally occurring arginine-depleting enzyme. The preparation of tissues and cells containing these enzymes can be minimal, and minimally processed tissues and cells are expected to be favored for that reason. The enzymes can also, however, be recombinantly or synthetically produced enzymes that correspond to the full-length naturally occurring enzyme or that are biologically active variants thereof. The biologically active variant can be an active fragment or other mutant (e.g., a substitution mutant) of a full-length, naturally occurring enzyme. An active variant is one that retains sufficient arginine-depleting activity to produce an effective therapeutic outcome (e.g., treatment of cancer in a patient and/or reduction of the plasma concentration of arginine in a patient to below about 10 µM (e.g., about 1 to 5 µM)).

As noted, naturally occurring arginine-depleting enzymes such as arginase are available from various sources, including animals, bacteria, and yeast. Accordingly, tissues from animals and preparations of cultured bacteria and yeast can be minimally processed into compositions for use in the present methods. Alternatively, recombinant or synthetic arginine-depleting enzymes can be produced by conventional methods known in the art and are also useful. For example, a host cell (e.g., a mammalian, bacterial or yeast cell) can be genetically transformed with a recombinant nucleic acid vector encoding an arginine-depleting enzyme. The cell or a cell lysate can then be used in the present methods. One could also collect the cells and purify the arginine-depleting enzyme. Guidance concerning recombinant DNA technology can be found in numerous well-known references, including Sambrook et al. (*Molecular Cloning-A Laboratory Manual*, Cold Spring Harbor Press; and Ausubel et al. (eds.), 1994, *Current Protocols in Molecular Biology*, John Wiley & Sons, Inc.).

One source of arginine-depleting enzymes (e.g., arginase) is liver from domestic animals (e.g., pigs, cows, oxen, horse and sheep) or wild animals (e.g., rodents). Human liver is another potential source of arginine-depleting enzymes, particularly if used as an autograft. For example, a patient's own liver surgically resected to remove a primary tumor or metastases can be used to prepare an arginase-containing extract for auto-transfusion.

The bacteria can be a *Lactobacillus* or *Escherichia* (e.g., *E. coli*), which may or may not be engineered to overexpress a relevant enzyme (e.g., an arginine-depleting enzyme). The thermophile *Bacillus caldovelox* can also be a source of a naturally occurring thermostable arginase (see, e.g., Patchett et al., *Biochim Biophys Acta*, 1077(3):291-298, 1991).

The fungal cell can be a yeast cell. Certain strains of baker's yeast (e.g., *S. cerevisiae*) possess significant endogenous arginase activity (see, e.g., Green et al., *J. Biol. Chem.* 265(3):1601-1607, 1990). Yeast cells can also be engineered to overexpress arginine-depleting enzymes using conventional methods known in the art.

Because the present compositions are designed for intestinal delivery, there is no risk of immune-based resistance to repeated treatments and much less concern about enzyme purity and preparation. The composition can be a simple liver extract from a domestic animal (which may be, but is not necessarily, supplemented as described herein (e.g., with lactate and/or pyridoxal phosphate)).

An arginine-depleting enzyme can be administered in intact cells, cell homogenates (including crude homogenates), cell lysates, or partially purified cell lysates. For example, intact mammalian, bacterial or yeast cells; mammalian, bacterial, or yeast cell homogenates; mammalian, bacterial or yeast cell lysates or partially purified lysates can be used. Preparations other than those in crude form can therefore be described as partially purified or concentrated, and any of the preparations can be sterilized.

Tissue extracts (e.g., liver extracts) and cell extracts can be obtained by conventional methods known in the art. The liver extract can be partially purified by heating the extract for 10 to 15 minutes at approximately 65° C. This will not substantially degrade the arginase-depleting enzyme, but will denature and precipitate many other proteins. Such a heating step can increase arginase as a percentage of the total protein in the liver extract by about three fold.

To prepare an extract with significant arginase activity within a reduced volume, one can concentrate the arginase by ultrafiltration or evaporation by heat or vacuum. Lyophylization is also an option, but this produces a formulation requiring reconstitution before use. Any of the preparations described above, particularly the crude preparations, homogenates, and lysates, can also be sterilized. Sterilization can be achieved in a variety of known ways. For example, the preparation can be filtered through a filter (e.g., a 0.2µ, or a 0.45µ, sterilization filter).

We have prepared pig liver extracts, and this process can be used to prepare the present compositions or as a guide for preparation of arginine-depleting enzymes from other sources.

One important and potentially the only necessary step in preparation of a liver extract is disruption of the hepatocytes in order to release arginase. This can be done by mechanical means (e.g. ultrasound, or high speed cutting/shearing) or by osmotic pressure. Further steps can be used to prepare an extract more suitable for further preparation, such as concentration, and/or for delivery. For example, a pig liver extract preparation process may include the following steps: (1) chopping, preferably on ice, a pig liver to small pieces, and homogenizing the liver pieces including cellular disruption; (2) optionally storing the homogenized liver on ice overnight; (3) centrifuging the homogenate at 4° C. for 10 minutes at 1000 to 20000 g, or until it separates into three distinct layers (a cellular debris layer, an aqueous layer and an oil/fatty layer); (4) separating the aqueous layer from the other layers; (5) heating the aqueous layer to 65° C. for 10 minutes; (6) centrifuging again at 4° C. for 10 to 20 minutes; (7) separating the aqueous layer from the sedimented layer, which contains mostly denatured, precipitated proteins; (8) concentrating the resulting liver extract (the aqueous layer) by vacuum or ultrafiltration (with a cutoff at 10000 to 30000 Daltons, below the molecular weight of liver arginase of about 35000 Daltons); (9) filter-sterilizing the extract on a non-pyrogenic filter (e.g., a 0.2 µm filter); and (10) packaging and storing the filtered extract at 4° C. It is also possible to heat the homogenized liver to 65° C. and do only a one step centrifugation, preferably at a higher temperature of up to 50° C.

The arginine-depleting enzymes and any other enzyme included in the present compositions or delivered by the present methods can be pegylated. While pegylation is possible, we do not expect it to be of any benefit when the enzyme is delivered to the intestine. With direct delivery into the circulation, e.g. by i.v. infusion, pegylation extends the half-life of the enzyme and decreases immunological response, but it also increases the risk of pancreatitis. Extending the half-life may reduce the dosage required, but an extension of half-life may not be desirable in the present methods, particularly toward the end of an acute treatment. After treatment, the goal is to reestablish normal arginine levels quickly so the proliferation of healthy cells can resume.

An arginine-depleting enzyme may require an essential co-factor (e.g. manganese for arginase). Natural arginases, e.g., arginase from an animal liver, seem to retain manganese much longer than recombinant enzymes and in most cases we did not need to reactivate the enzyme even after prolonged (several weeks) storage at 4° C. Recombinant versions we have used lost much of the activity which could be restored by heating the enzyme in solution to 60° C. in the presence of manganese.

To help protect the integrity of the arginine-depleting enzyme, inhibitors of proteolytic enzymes can be added to the liver extract (e.g. soybean proteases inhibitors (van Den Hout et al., *J. Agric. Food Chem.* 46(1):281-285, 1998; Wan et al., *Cancer Epidemiol. Biomarkers Prev.* 9(7):741-747, 2000; Csáky and Fekete, *Acta Vet Hung.* 52(3):299-313, 2004). Pharmacological inhibitors of pancreatic secretion can also be used to minimize the loss of the activity of arginine depleting enzymes.

In any control experiments one wishes to conduct, a test group can receive a preparation in which the arginine-depleting enzyme has been destroyed by heating the preparation to 100° C. for at least 10 minutes.

Ornithine Depleting Enzymes: An ornithine-depleting enzyme can also be included in the arginine-depleting enzyme composition and/or administered in the present methods. Evidence suggests that certain cancer cells can use ornithine as a substitute for arginine (see, e.g., Ikemoto et al., *Biochem J.* 270(3):697-703, 1990).

Naturally occurring ornithine-depleting enzymes (e.g., an ornithine decarboxylase) are available from various sources known in the art. These sources include certain bacterial cells (i.e., bacterial cells that express an ornithine decarboxylase). Administering an ornithine-depleting enzyme by way of intact bacterial cells only marginally affects the enzyme's activity and offers the potential of in situ proliferation of the bacterium, which may have protective value for intestinal flora.

Recombinant or synthetic ornithine-depleting enzymes can also be produced by conventional methods known in the art. For example, lactobacilli are a source of naturally occurring ornithine-depleting enzymes (e.g., ornithine decarboxylase) and these bacteria can also be engineered to overexpress an ornithine decarboxylase by inclusion of a suitable nucleic acid vector.

The ornithine-depleting enzyme can be purified or partially purified or delivered in intact cells, cell homogenates, cell lysates, or partially purified cell lysates. Any of the preparations may be sterilized.

Pyridoxal phosphate, which is an essential co-factor of ornithine decarboxylase, may be co-administered whenever an ornithine decarboxylase is administered. This co-factor is also present in liver and plasma, the concentration in liver being about 100 times higher than in the plasma (see Furth-Walker et al., *J. Nutr.* 120(11):1338-1343, 1990). Despite this higher concentration, even more pyridoxal phosphate may be required in the present compositions and methods. Therefore, supplementation to the millimolar range may be advisable; effective enzyme inhibition may call for a concentration of pyridoxal phosphate in the millimolar range (i.e., at least 1 millimolar).

More generally, where an arginase is used to convert arginine to ornithine, it may be beneficial to remove the resulting ornithine, and this can be achieved with ornithine decarboxylase.

Inhibitors of Endogenous Arginine Production: Inhibitors of endogenous arginine production from the intestinal-renal axis can also be included in the present compositions and delivered by the methods described herein. The intestinal-renal axis is a biochemical pathway for endogenous production of arginine, whereby citrulline is produced in the small intestine from the non-essential amino acids proline, glutamine or glutamate via ornithine and then converted to arginine primarily by the kidneys.

Such inhibitors can include any agents (e.g., a compound or drug) that inhibit a step in the biochemical pathway that constitutes the intestinal-renal axis whereby arginine is produced. Exemplary inhibitors useful for the present compositions and methods include, but are not limited to, pyridoxal phosphate, lactate, Gly-Gly-PALO, and gabaculine. Pyridoxal phosphate is an inhibitor of the conversion of glutamine or glutamate to ornithine. Lactate inhibits the conversion of pro line to ornithine. Gly-Gly PALO inhibits the conversion of ornithine to citrulline. Use of gabaculine (3-amino-2,3-dihydrobenzoic acid), a known inhibitor of ornithine aminotransferase, an enzyme converting pyrroline-5-carboxylate (P5C) to ornithine in the common path of the citrulline synthesis from both proline and glutamine substrates, is also an option in inhibition of citrulline synthesis, but used in vivo it has, paradoxically, led to an increase of circulating ornithine (Wu et al., *J. Nutr.* 27(12):2342-2349, 1997; Alonso and Rubio, *Biochem J.* 259(1):131-138, 1989). Use of gabaculine is thus limited to those cancer types which could not substitute ornithine for arginine.

These inhibitors can be readily obtained from commercial sources and added to the compositions described herein.

Another target for inhibition of the intestinal-renal axis is the conversion of proline to ornithine in the intestine and the preferred inhibitor is lactate. Liver also contains a relatively high concentration of lactate. For example, liver extracts that have not been diluted or concentrated may contain lactate at several times that of the normal plasma level (1 mM). Liver is also rich in pyridoxal phosphate, an inhibitor of P5C synthase. Accordingly, liver extracts, delivered using methods described herein, can be used to inhibit endogenous arginine production from the intestinal-renal axis.

The present compositions can contain about 5 to 30 mM (e.g., about 5, 10, 15, 25 or 30 mM) of lactate and at least or about 1 mM of pyridoxal phosphate.

Antibiotics: It may be useful for the present compositions and methods to modify the micro flora of the small intestine to reduce the population of arginine-producing bacteria therein. Intestinal bacteria can be a significant source of arginine. At various times during the treatment regime (e.g., prior to administering an arginine-depleting enzyme and increasing lactate for arginine depletion), the intestine can be sterilized by antibiotics and preferably by non-absorbing antibiotics (i.e., those which remain in the intestinal lumen after oral delivery such as gentamicin and vancomycin).

Accordingly, antibiotics such as gentamicin and vancomycin, teicoplanin, neomycin, netilmicin, and amikacin, can be administered alone or in combination to the patients being treated with the compositions and methods described herein.

Antiemesis: Arginine deficiency has been linked to emesis in dogs (Burns et al., *J. Nutr.* 111: 1020-1024, 1981) and we have regularly observed it in most of the experimental dogs. The recommended treatment is with metoclopramide.

Dietary Restrictions and Supplements: For the compositions and methods described herein, it may be beneficial to further limit exogenous sources of arginine such as proteins or amino acids that would be consumed in food and drinks.

Accordingly, a patient's diet can be modified as part of the present methods so that arginine consumption is limited. For example, the patient can receive amino acid or protein-based supplements that lack arginine but include one or more of: leucine, isoleucine, histidine, phenylalanine, tryptophan, threonine, valine, lysine and methionine.

Alternatively or in addition to providing a mixture of individual amino acids one can provide a hydrolysate of casein, the predominant phosphoprotein in milk and cheese. Casein can be hydrolyzed to individual amino acids either by enzymes or by an acid. Casein is relatively low in arginine. If mixed with an arginine depleting enzyme, for example, arginase, some time before administration, arginine would be converted by the time of delivery. Any arginine present would be converted to ornithine, which cannot be absorbed by the small intestine.

Support with arginine-free amino acid mix NepfrAmine® (Braun Medical Inc.) of 1 g/kg/day can be added to the parenteral feeding tube or it can be delivered i.v.

To maintain normal intestinal function, a non-metabolizing substance, e.g. cellulose or inulin, can be included in the present compositions and administered in the methods described herein.

To maintain normal body fluid balance and plasma ions, infusion of physiological electrolytes, e.g. Ringer's solution, can also be administered with the compositions and methods described herein.

Inhibitors of Protein Breakdown: It is not a simple matter to extrapolate from studies of arginine deprivation in culture to in vivo methods. In response to deprivation in vivo, homeostatic responses at the systemic level initiate protein breakdown, mostly of muscle tissue, in order to replenish arginine to its base-line level (of about 80 to 140 µM in plasma, in both humans and dogs). Where arginine is purposefully and aggressively depleted, life-threatening conditions can arise due, at least in part, to the accumulation of ammonia. A vicious cycle can result, where reduction of arginine concentration leads to increased generation of ammonia, which triggers the release of arginine from endogenous stores, which will be depleted by the enzymatic intervention of the present methods, which results in the accumulation of more ammonia, and so on. The solution to this problem lies in damping the usual homeostatic response as described above (see also Tepic and Pyk, U.S. Pat. No. 6,261,557).

Accordingly, the compositions and methods described herein can also include an inhibitor of protein breakdown. Agents that inhibit protein breakdown are known in the art. They include, e.g., insulin, an insulin-like growth factor (e.g., IGF-I or IGF-II), or growth hormone. These agents are readily available from various commercial sources. For example, the fast-acting insulin solution ACTRAPID® is available from Novo Nordisk. A recombinant human IGF-I INCRELEX® is available from Tercica (Brisbane, Calif.).

Administering insulin to inhibit protein breakdown can lead to hypoglycemia, which may necessitate administration of one or more sugars such as glucose, dextrose, or fructose. Accordingly, the present compositions can include one or more such sugars, and the present methods can include administering one or more such sugars.

These agents can be administered either as part of a composition that contains an arginine-depleting enzyme or separately.

The use of insulin helps achieve systemic, deep and sustained arginine depletion in vivo. Insulin stimulates production of proteins and inhibits their breakdown, the net effect leading to intended reduction of free arginine. Use of insulin calls for an increased intake of sugar in order to maintain normal levels of blood glucose. Although IGF-I is an even more potent growth factor than insulin, its effect on glucose is less pronounced (Douglas et al., *J. Clin. Invest.* 88:614-622, 1991). INCRELEX® (Tercica) was approved by the U.S. Food and Drug Administration as a replacement therapy for severe primary IGF-I deficiency and can be used in the present compositions and methods.

In vitro, we have shown that the addition of IGF-I to leukemia cell cultures placed in arginine-free medium leads to complete elimination within three days of even the most tenacious, rare survivors of arginine depletion alone.

Use of IGF-I complexed with its principal binding protein, IGFBP-3, has been shown even more effective in reversing catabolic state and more tolerant in dosing than IGF-I (Hendon et al., *Annals of Surg.* 229(5):713-722, 1999). Accordingly, IGF-I complexed with IGFBP-3 can be administered in the context of the present methods and included in the present compositions.

In terms of dosages, the following can be used as guidance. For example, 13.7 mg/kg/min, or 20 g/kg/day, of glucose, can be administered to human patients with 4 mI.E./kg/min insulin infusion (or approximately 6 I.E./kg/day). At high physiologic rates of 1 mI.E./kg/min, or 1.5 I.E./kg/day of insulin, glucose can be administered at 8.7 mg/kg/min, or 12.5 g/kg/day. In dogs, for example, under 12 I.E./kg/day insulin infusion, 20 g/kg/day or infusion of 50% glucose at a rate of approximately 30 ml/h for a dog of 18 kg body weight can be administered to maintain normal plasma glucose levels.

Nitric Oxide Donors: Depletion of arginine also suppresses NO production, and the ensuing platelet activation can lead to clot formation, loss of platelets and internal bleeding. In the healthy experimental dogs we have worked with, bleeding has been observed by the second or third day of arginine depletion. There is also an increased risk of generalized, rapid platelet activation, which may lead to disseminated intravascular coagulation (DIC). This condition is difficult to treat and can be life-threatening. We propose to restore systemic levels of NO by delivery of an NO donor (e.g., one or more of the known NO donors: sodium nitroprusside (SNP), nitroglycerin or isosorbide dinitrate (ISDN)). ISDN formulations for percutaneous delivery are commonly available and preferred over other delivery modalities, so ISDN could be alternated with nitroglycerine, delivered percutaneously as well. As restoring NO in an arginine depleted state can lead to excessive vasodilatation (since all of the pressor peptides, which would normally counterbalance the vasodilation, contain arginine and thus may not be produced as required), we propose supplying a pressor peptide. One could use vasopressin or one of its more stable analogs, such as ornipressin, terlipressin or desmopressin. Sodium nitroprusside releases cyanide that can reach toxic levels, especially in dogs and during a prolonged treatment. Thus, SNP use should be always accompanied by an antidote to cyanide, e.g. a vitamin precursor B12a or sodium thiosulfate.

Pressor Peptides: As noted, the present compositions can also include a pressor peptide, and the present methods can include administering a pressor peptide in admixture with other medications for i.v. delivery or by way of a separate formulation.

Pressor peptides contain arginine, and therefore, may not be produced at a normal rate in an arginine depleted state. In some instances, it may thus be useful for the present compositions and methods to include a pressor peptide (e.g., vasopressin, ornipressin, or terlipressin). These known pressor peptides are available commercially and can be administered intravenously, subcutaneously, or intramuscularly. Other routes of administration (e.g., nasal delivery or eye drops) can also be used.

There are several approved analogs of the natural vasopressin peptide. In most of our experiments on dogs, GLYPRESSIN® (terlipressin) from Ferring was used; for several dogs and for mice, ornipressin (POR 8® also from Ferring) was selected for its generally more effective pressor function in comparison to GLYPRESSIN® (which has a relatively stronger anti-diuretic effect).

POR 8® is supplied in solution with 5 I.E./ml. Due to limited capacity of the osmotic micro pump, for the mice experiments, POR 8® was concentrated by factor two (using evaporation) and delivered at the rate of (12 microliters/day× 10 I.E./1000 microliters)/0.02 kg of body weight=6 I.E./kg/day.

In the United States, there are several FDA-approved vasopressin drugs. We plan to use the generic compound from American Regent Laboratories in which 0.5 ml of solution contains 10 units of vasopressin.

For the dogs this would translate into 1 I.E./kg/day. This is delivered with the dose of SNP of 1.8 micrograms/kg/min, so for the planned dose of SNP of 1 microgram/kg/min the rate of vasopressin should be approximately 0.6 I.E./kg/day. For a 20 kg dog this would be 12 I.E./day, or 0.6 ml/day of generic vasopressin from American Regent Laboratories.

In dogs, terlipressin was used at typically 0.13 mg/kg/day. Since 1 mg of terlipressin corresponds to approximately 5 I.E. of ornipressin, this would be equivalent to the dose used in mice.

For comparison, for i/v. infusion in esophageal bleeding in humans, 20 I.E. of ornipressin are diluted in 100 ml of saline and infused over 20 minutes. This can be repeated several times, as needed. Thus, the suggested dose of 12 I.E./day for a 20 kg dog is within the normal pharmacologic range. Administration of vasopressin is to be adjusted as needed to balance vasodilatory effects of SNP and is best adjusted by keeping the pulse rate normal. SNP will raise the pulse; vasopressin will lower it. It is recommended to increase the SNP delivery rate in several steps, adjusting vasopressin infusion at each step to lower the pulse back to normal. Small bolus injections of vasopressin would be more in line with the manufacturer's recommendations (instead of continuous).

A generic form of vasopressin, available in certain countries, can be used s.c. or i.m., or alternatively, intranasal on cotton pledges. Such applications in 2 to 4 hour intervals may well be used to balance out the effects of NO.

Diuretic: High infusion rates, use of NO donor and of vasopressin may result in unwanted fluid retention, which can be controlled by a suitable diuretic, e.g. furosemide (Furosemide, 10 mg/ml, from INTL MEDICATION).

Prostacycline: Strict arginine depletion can also suppress prostacycline in an indirect way, and this may lead to platelet activation and all of the sequelae. Our recommendation here is the administration of prostacycline or one of its more stable analogs, such as iloprost (Tepic, U.S. Application No. 60/350, 971).

A prostacycline or its analog can be included in the present compositions and administered by the methods described herein. In some instances, prostacycline or its stable analog, iloprost, can be administered to a patient being treated with the present compositions or methods to prevent activation and loss of thrombocytes. In shorter treatment sessions (e.g., acute arginine-depleting session of up to about three days), prostacycline may not be needed.

Patients Amenable to Treatment: The present compositions and methods can be used to treat patients diagnosed with cancer, for example, cancer of the blood, liver, breast, bone, lung, pancreas, skin, reproductive system, brain, soft connective tissue, or gastrointestinal tract. The present compositions can also be used in the preparation of a medicament (e.g., a medicament for the treatment of cancer, particularly arginine dependent cancers).

While the present compositions and methods can be used to treat any type of cancer in any patient, certain types of cancer may be more sensitive to arginine depletion, and therefore, particularly suitable for the treatments described herein. For example, hepatocellular carcinoma (HCC) may be particularly amenable to treatment (see, e.g., Curley et al., *Hepato-Gastroenterology* 50:1208-1211, 2003).

HCC is very sensitive to arginine depletion and, perhaps not unrelated to its sensitivity, rich in arginase. When the first cells die within the tumor, arginase will be released and will cause a further local depletion of arginine, making it even more difficult for the remaining cells to survive. Another aspect of the unusual sensitivity of HCC to arginine depletion is its reduced ability to substitute citrulline for arginine due to its, paradoxically, generally low expression of argininosuccinate synthetase, an enzyme required for conversion of citrulline into arginine. However, arginine deiminase greatly increases systemic concentrations of citrulline and, even in the case of HCC, there will likely be a sub-population capable of converting citrulline to arginine and thus leading to resistance to further treatment. The advantage of the approach disclosed here, in addition to its relying on simple, common substances, is that not only arginine, but also ornithine and citrulline are suppressed and it thus offers a possibility of treating a wide range of cancers. Current estimates suggest as many as eight in ten cancer types are susceptible to arginine depletion. Furthermore, our own in vitro work has suggested that deploying IGF-I in arginine depleted states can eliminate even the most tenacious survivors of arginine depletion (in our experiments, leukemia cells). Our most current in vitro work suggests that using native liver arginase, rather than the recombinant type, to deplete leukemia cells of arginine results it a total kill. While some cells did not break up, they were unable to proliferate when placed in full medium even after 40 days.

HCC is the predominant type of liver cancer, accounting for about 90% of all cases of primary liver cancer. Hepatitis B and C are considered main causative factors. HCC is endemic in many Asian and African countries, accounting for perhaps as many as 1.3 million annual cancer deaths worldwide.

Another type of cancer that is particularly sensitive to arginine depletion is melanoma. This is a highly invasive cancer, usually of cutaneous origin. Excessive exposure to sunlight is a major risk factor, and the most important factor in the rapidly rising incidence of melanoma. Early surgical treatment is very effective, as the overall 5-year survival rate is about 80%. As noted, melanomas are very sensitive to arginine depletion and generally unable to substitute citrulline for arginine because they fail to produce the required enzymes (ASS and ASL).

As simple or crude preparations of an arginine-depleting enzyme (e.g., a crude liver extract or other impure preparation that would not be suitable for administration by an intravenous, intramuscular, intraperitoneal or subcutaneous route) can be used in the present methods and compositions, patients in the undeveloped regions of the world may particularly benefit from the treatments described herein. For example, patients with hepatocellular carcinoma in far east Asia and sub-saharan Africa are suitable patients for the affordable treatment methods described herein.

The compositions and methods described here can also be used for treating patients who have undergone or who will undergo other cancer therapies (e.g., radiation therapy, chemotherapy or surgery). In some instances, the present compositions or methods can be used to treat a patient before or after the patient has finished a course of radiation therapy or chemotherapy, or before or after undergoing surgery to remove a tumor. In other instances, the present methods or compositions can be administered concurrently with one or more other cancer treatments. Normal cells can respond to arginine depletion by exiting into rest phase, where they can be more resistant to radiation therapy or chemotherapy. Thus, in some cases, the present methods and compositions can be employed concurrently with extreme radiation treatment or chemotherapy to treat a cancer patient.

The term "patient" is used throughout the specification to describe any animal (whether human or non-human, such as a domesticated animal kept as a pet or as livestock) to whom treatment according to the methods of the present invention is provided. Veterinary and non-veterinary applications are clearly contemplated. The term includes, but is not limited to, birds, reptiles, amphibians, and mammals (e.g., humans, other primates, pigs, rodents such as mice and rats, rabbits, guinea pigs, hamsters, cows, horses, cats, dogs, sheep and goats).

Route of Administration and Dosage: The present compositions can be delivered directly to a patient's small intestine by conventional methods known in the art. For example, delivery of the present compositions can be facilitated by a nasointestinal feeding tube, or a feeding tube inserted through a jejunostomy, esophagostomy, or gastrostomy. A pump can be used to control and achieve continuous delivery of the desired dosage. It may also be advantageous to bypass delivery of the present composition to the duodenum to minimize production and excretion of pancreatic enzymes, which can degrade arginine-depleting enzymes. Other methods that bring the present compositions directly into contact with the small intestine without passing through the mouth, rectum, or circulation can be used. Alternatively, the compositions can be protected from degradation in the upper portions of the alimentary canal by encapsulation using methods known in the art and, thus, can be administered to the small intestine by oral administration.

Administration "directly to the lumen of the patient's small intestine" means that the composition being administered is brought into contact with the lumen of the small intestine, without being negatively affected, e.g. denatured, by passing through another part of the alimentary canal (e.g., the acidic environment of the stomach).

As a further protective measure, inhibitors of proteolytic enzymes can be added to the composition (e.g., a liver extract or other liver preparation, optionally supplemented with one or more of the agents described above). For example, soybean protease inhibitors can be included (van Den Hout et al., *J. Agric. Food Chem.* 46(1):281-285, 1998; Wan et al., *Cancer Epidemiol. Biomarkers Prev.* 9(7):741-747, 2000; Csáky and Fekete, Acta Vet. Hung. 52(3):299-313, 2004). Pharmacological inhibitors of pancreatic secretion can also be used to minimize the loss of arginase activity.

Other agents, compounds or drugs useful for the methods described herein can also be administered by conventional methods or according to the recommended guideline for that agent, compound or drug. Examples of routes of administration for the supplementary agents (i.e., not the arginine-depleting enzyme composition) include parenteral (e.g., intravenous, intradermal, subcutaneous, by inhalation, transdermal (topical), transmucosal, and rectal administration) and oral administration.

Effective amounts of the arginine-depleting enzyme compositions used in the present methods can include, for example, amounts that are sufficient to reduce the plasma concentration of arginine to below 10 micromolar (10 µM), e.g., about 1 µM, below about 5 µM, or between about 2 µM and about 9 µM. An effective amount can also be an amount that is sufficient to reduce the size of a tumor in a patient, inhibit tumor growth in a patient, or generally improve the prognosis of a patient diagnosed with a cancer. For the primary compositions described herein, an effective dosage of an arginine-depleting enzyme can be administered at a rate equal to or higher than 200 units per kilogram of body weight per day (e.g., about 200 units per kilogram of body weight per day, between 200 and 2000 units per kilogram of body weight per day, or between 2000 and 20000 units per kilogram of body weight per day). Since the direct delivery of the enzyme to the intestinal lumen does not, in itself, result in any toxicity, the dosage depends on the targeted levels of arginine in circulation.

The present compositions can be administered in one or multiple sessions, each of the sessions lasting between one and eight days. Since there is no evidence of resistance to repeated arginine depletion treatments, these sessions can be repeated within weeks or months, if and as needed. For certain cancers it may also be desirable to have two or more sessions repeated with a short break (hours to days) between them. These breaks may push the cancerous cells through the cycle, making them vulnerable to the next depletion period, while the normal cells would remain dormant.

Skilled practitioners can readily appreciate that certain factors influence the dosage and timing required to effectively treat a patient, including but not limited to the characteristics of the patient to be treated, the severity of the cancer or tumor, previous treatments, the general health and/or age of the patient, and other disorders present.

Plasma levels of arginine, ornithine and citrulline can be measured throughout treatment in an amino acid analyzer. Blood samples (e.g., about 2 ml) can be taken about every eight to twelve hours.

EXAMPLES

Figure 1:
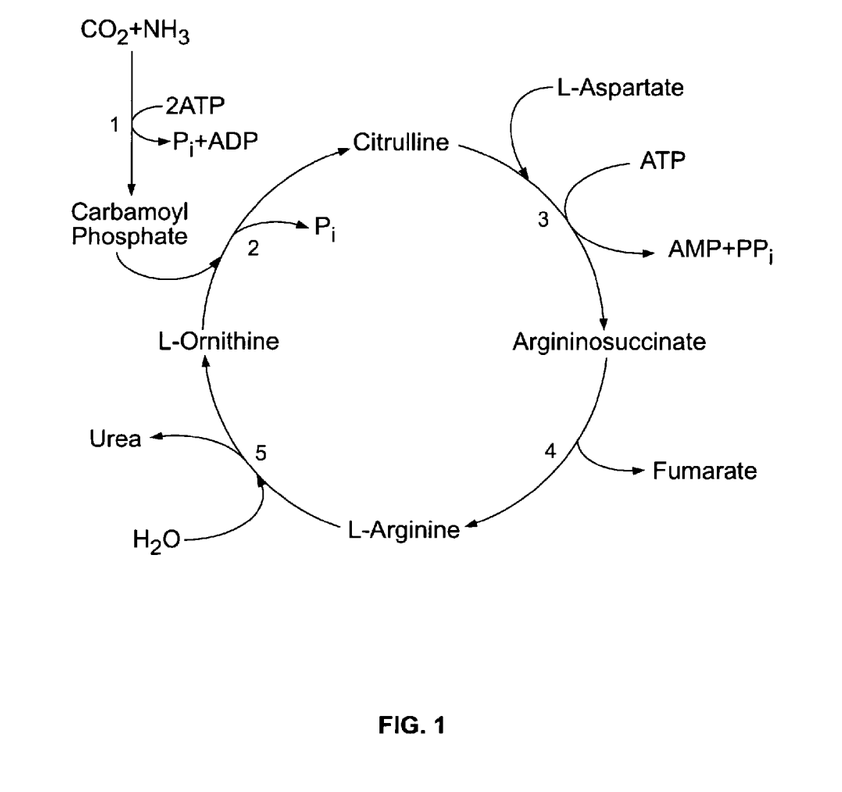
FIG. 1 is a diagram illustrating the urea cycle, which catalyzes the conversion of ammonia to urea and is the dominant path for elimination of excess nitrogen. The enzymes involved in the various reactions are indicated by the numbers 1-5, which represent, respectively, carbamoylphosphate synthase (1); ornithine carbamoyltransferase (2); argininosuccinate synthase (3); argininosuccinate lyase (4); and arginase (5).
Figure 2:
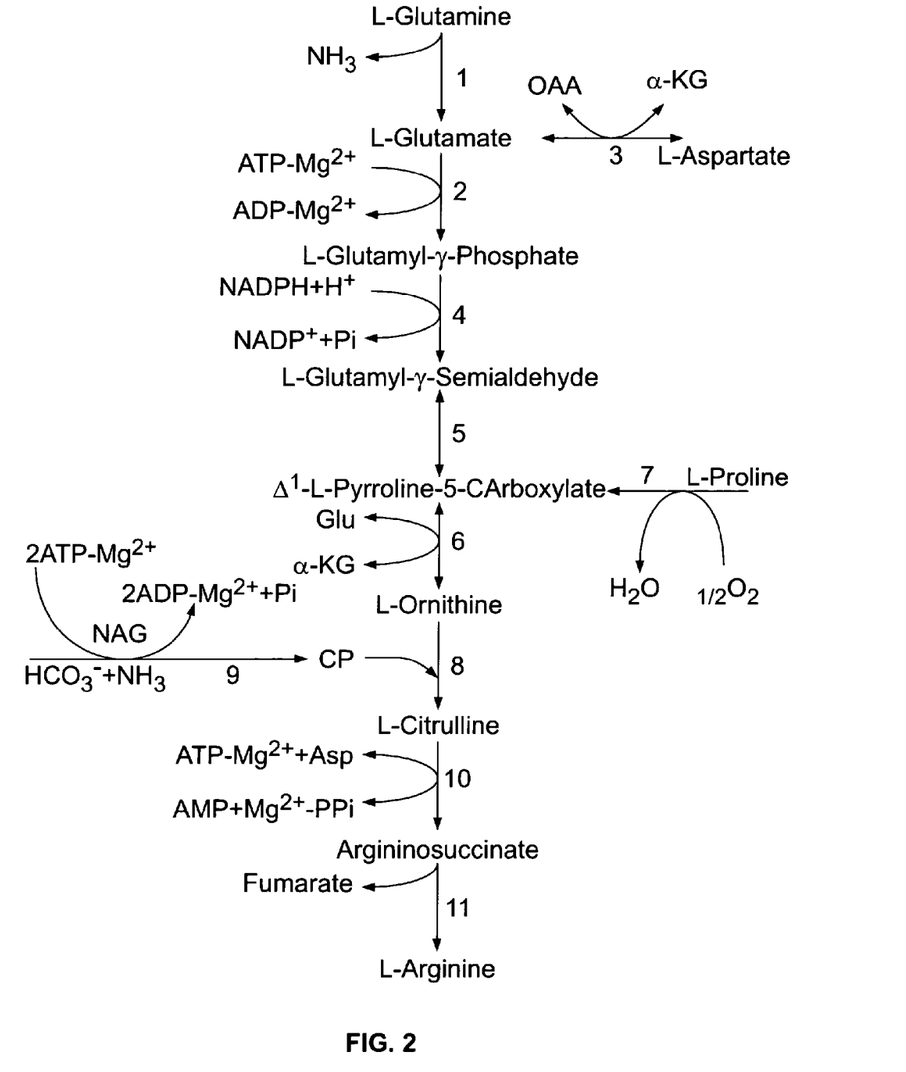
Figure 3:
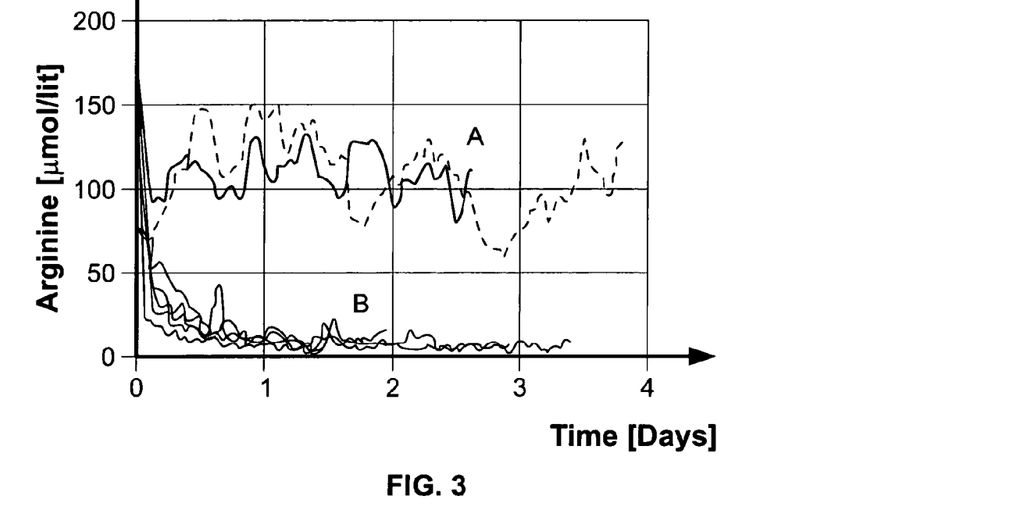
FIG. 3 is a line graph showing plasma concentrations of arginine (in micromoles per liter) over time (days) in several experimental dogs subjected to arginine depletion by selective hemodialysis. The animals in Group A (two animals) did not receive insulin. The animals in Group B (five animals) received insulin-glucose clamp.

Administration of Insulin to Facilitate Arginine Depletion and Varying Arginase Concentrations: We subjected dogs to arginine depletion by selective hemodialysis. More specifically, the blood was dialyzed against a mixture of amino acids other than arginine, ornithine and citrulline, in a solution that also contained water soluble vitamins, electrolytes and glucose at physiological concentrations. The dogs were divided into two groups. Those in Group A (two animals; many other sessions were performed with the same outcome) did not receive insulin and those in Group B (five animals) received insulin-glucose clamp. Plasma concentrations of arginine were obtained over time. As shown in FIG. 3, arginine could not be lowered without insulin much below its normal level but could be consistently lowered with insulin to about 10 micromolar (ten times below the normal concentration).

Figure 4:
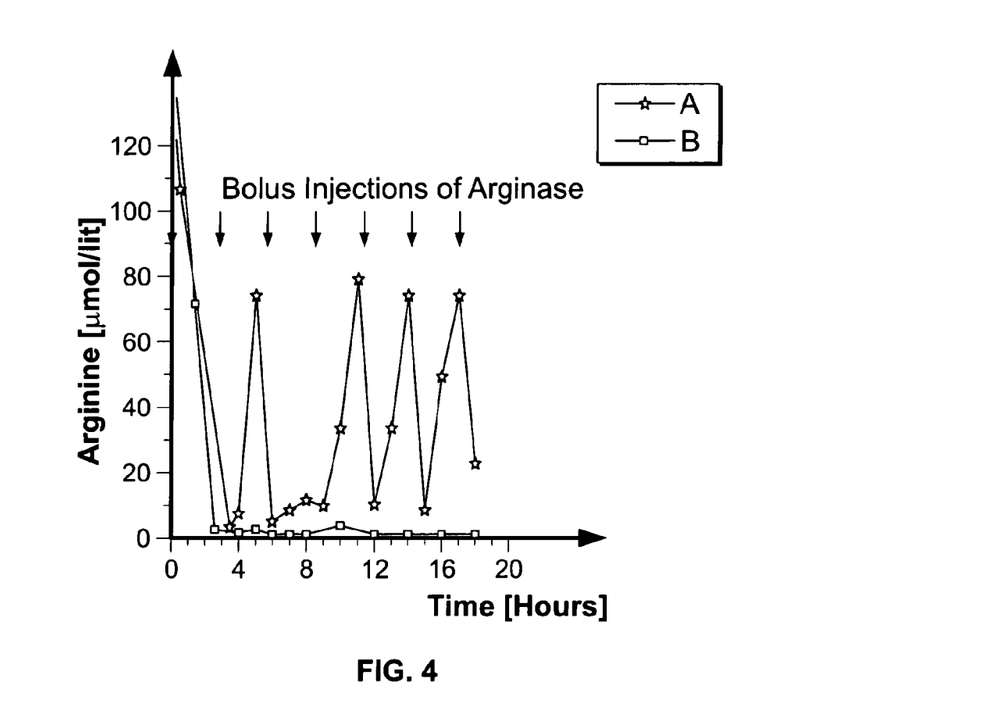
FIG. 4 is a line graph showing plasma concentrations of arginine (in micromoles per liter) over time (hours) in two experimental dogs subjected to arginine depletion by bolus intravenous administration of liver extracts. The intravenous infusions were delivered without insulin to the animal A and with insulin-glucose to the animal B.

In another series of experiments, plasma concentrations of arginine were measured over time in dogs subjected to arginine depletion by way of an autologous infusion of liver extract. All animals were anesthetized throughout the preparation and administration of the liver extract (one liver lobe was surgically removed and used to prepare the liver extract for subsequent administration). In a pilot experiment, bolus intravenous infusions were delivered without (Animal A) or with insulin-glucose (Animal B). The total dose administered to both dogs corresponded to 3 g of liver per kg body weight per day, or approximately 1000 units of arginase per kg body weight per day. As shown in FIG. 4, arginine levels fluctuated dramatically in Animal A but were maintained at a consistently low level in Animal B. Insulin was continuously infused at 6 units per kg per day. Glucose was administered as needed to maintain normal plasma levels of 4 to 6 mM.

We also tested various infusion rates/dosages in dogs that were treated with insulin. The rate of 3 units per kg per day in most dogs was sufficient to maintain low arginine levels. At above 12 units per kg per day there was no further reduction of plasma arginine concentration.

Figure 5:
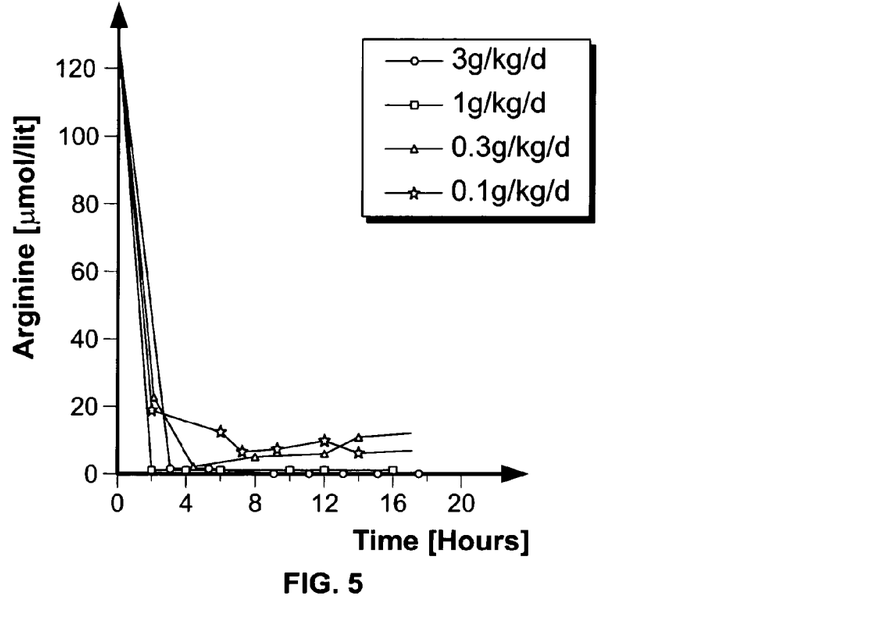
FIG. 5 is a line graph showing plasma concentrations of arginine (in micromoles per liter) over time (hours) in experimental dogs subjected to arginine depletion by continuous infusion of autologous liver extract. Continuous intravenous infusions were delivered at four different rates (3.0 g; 1.0 g; 0.3 g; and 0.1 g of liver/kg body weight/day, or approximately 1000; 330; 100; and 30 units of arginase/kg body weight/day, respectively) together with insulin-glucose.

In a follow up experiment, plasma concentrations of arginine were measured in four dogs subjected to arginine depletion by continuous infusion of autologous liver extract, by an intravenous route at four different rates: 3.0 g, 1.0 g, 0.3 g, and 0.1 g of liver per kg body weight per day. This is the equivalent of approximately 1000, 330, 110, and 30 units of arginase per kg of body weight per day, respectively. As shown in FIG. 5, the two highest rates of infusion lowered plasma arginine levels to about the limit of detection (i.e., ~1 μM). The very low levels of arginine achieved in these dogs have not been repeated in animals that did not have a fresh liver resection in order to collect the tissue for preparation of the extract. Subsequently we have attributed this success to a very likely inhibitory effect of the increased lactate (caused by the fresh liver resection) on the intestinal-renal axis.

Figure 6:
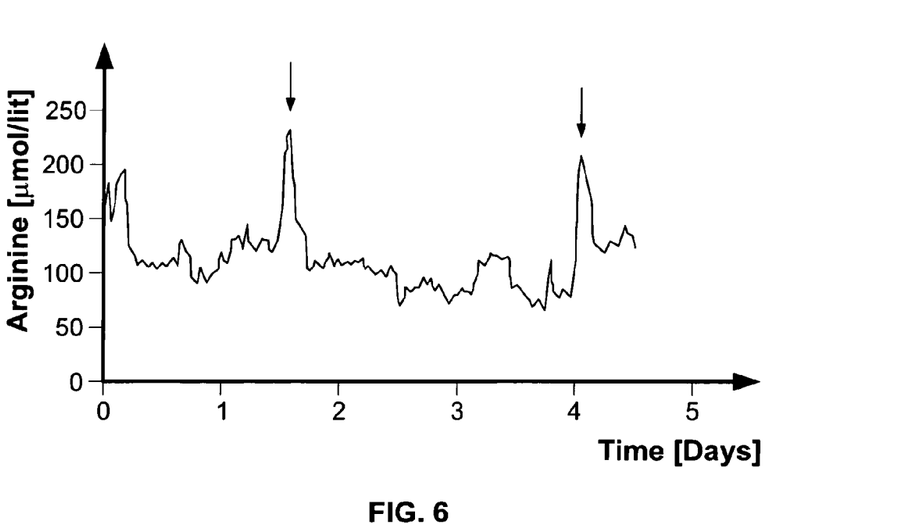
FIG. 6 is a line graph showing arginine levels resulting from a five-day session of arginine depletion by extracorporeal conversion of arginine to ornithine by arginase isolated behind a dialysis filter. No reduction of plasma arginine could be effectively achieved.

Extracorporeal Conversion of Arginine to Ornithine is Ineffective in Substantially Lowering Plasma Levels of Arginine: Over the course of a five-day session, we attempted to deplete arginine by extracorporeal conversion to ornithine behind a dialysis filter. As shown in FIG. 6, no significant reduction in the concentration of arginine in the plasma could be achieved. The two peaks in plasma arginine levels were due to the dog's consumption of two inadvertently offered collagen-rich snacks.

Figure 7:
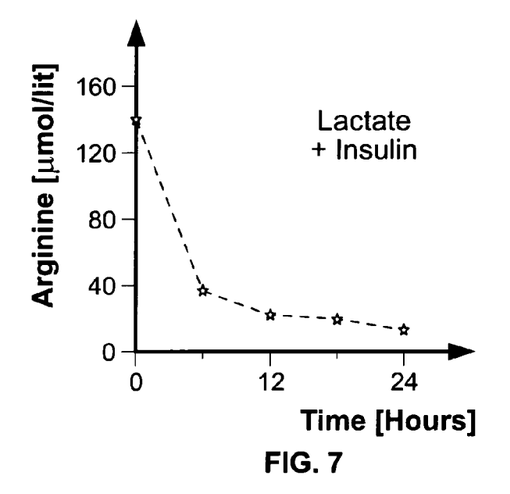
FIG. 7 is a line graph showing arginine levels resulting from i.v. infusion of a mixture of lactic acid and sodium lactate plus insulin.

Inhibition of the intestinal-renal axis: As commented above, we believe the result shown in FIG. 5 (i.e., a reduction in arginine to around the minimum level detectable) is due, at least in part, to the likelihood that lactate was produced following resection of the liver as well as to the presence of lactate in the administered extract itself. Lactate inhibits an arm of the intestinal-renal axis. As shown in FIG. 7, arginine depletion results from an intravenous infusion of lactic acid and sodium lactate. The ratio of these two agents was adjusted continually to maintain physiological pH levels in the blood, and an insulin-glucose clamp was administered concurrently.

Figure 8:
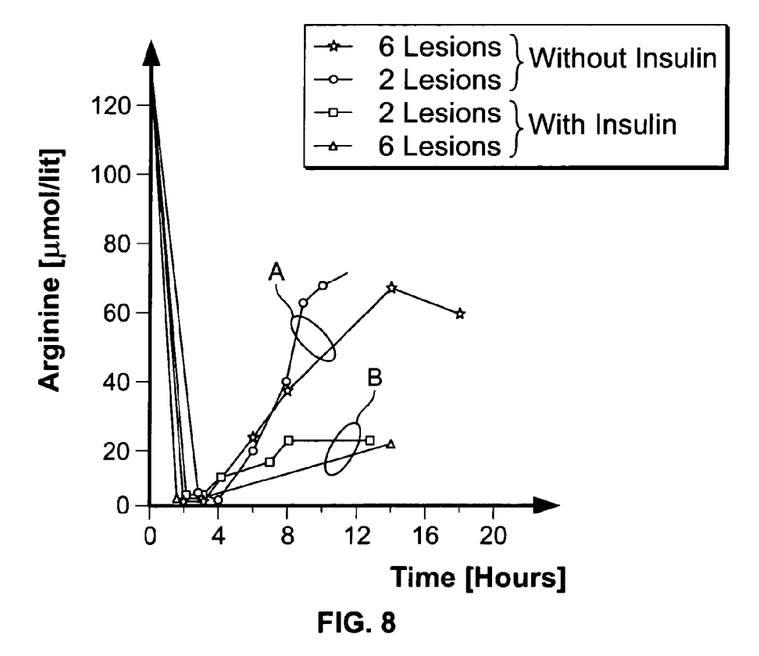
FIG. 8 is a line graph showing arginine concentrations in experimental dogs subjected to cryoablation of liver, simulating such procedures being performed for isolated, unresectable metastases of colon cancer. Group A (two animals) did not receive insulin; Group B (two animals) did receive insulin-glucose clamp.

Depletion of Arginine by Release of Arginase from Cryoablated Liver: Cryoablation may be performed to treat isolated and unresectable metastases of colon cancer. In one experiment, arginine concentrations were measured in dogs subjected to cyroablation of the liver. Those in Group A (2 animals) underwent cryoablation without administration of insulin while those in Group B (2 animals) underwent cryoablation with insulin-glucose clamp. As shown in FIG. 8, the resulting arginine depletion was transient in both groups. We believe this was due to the limited and transient release of arginase from the ablated lesions.

In vitro study of L1210 cells: We carried out in vitro studies with L1210 cells (of the mouse leukemia cell line). When grown in an arginine rich medium (1000 μM) subjected to arginine conversion by addition of pegylated human liver recombinant arginase, the cells stopped proliferating, but did not die for up to six days, suggesting that, at that concentration of arginine, ornithine can keep the cells alive. When placed in an arginine-free medium, up to 90% of the cells died and, when placed in an arginine-free medium with added arginase, up to 99% of the cells died. Most significantly, when the cells were placed in arginine-free medium with arginase and IGF-I, all of the cells died.

Figure 9:
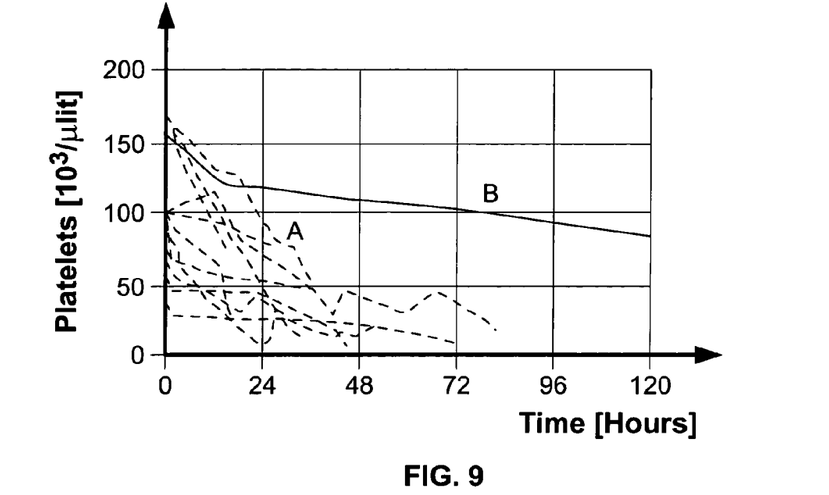

Inhibition of platelet activation: Platelets can be lost following arginine depletion. In a platelet activation study, we examined platelet levels in experimental dogs subjected to arginine depletion. The animals were divided into two groups. The dogs in Group A did not receive any NO donor.

The dog in Group B was placed on dialysis and an NO donor, SNP and prostacycline were continuously infused together with vasopressin to offset the effect of NO on vascular tone. The dog in Group B experienced only a modest platelet loss during a five-day session. Loss of platelets using the same measures has been successfully avoided in many subsequent sessions using infusions of an arginine-depleting enzyme.

Figure 10:
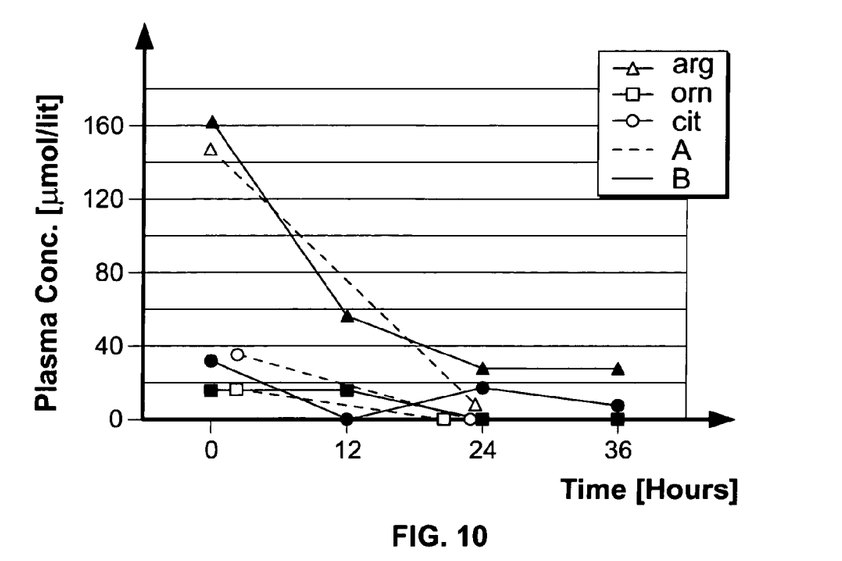
FIG. 10 is a line graph showing reductions of plasma arginine, ornithine and citrulline in two dogs treated with liver extract delivered directly to the small intestine. Dog A received approximately 3000 U/kg/day; dog B received approximately 400 U/kg/day.

Delivery directly to the small intestine: As shown in FIG. 10, plasma levels of arginine, ornithine and citrulline were reduced in two dogs treated with liver extract delivered directly to the small intestine. The dog A received approximately 3000 U/kg/day and the dog B received approximately 400 U/kg/day. We have never observed such low levels of ornithine or citrulline in dogs treated by intravenous infusions.

Treatment of dogs with cancer: While most of our experiments have been conducted on healthy experimental dogs, several were also carried out on dogs with cancer. In three cases, arginine was maintained at levels low enough to evoke an observable tumor response. In one dog with lymphoma, after about a day of low arginine achieved by intravenous infusion of a liver extract, we observed approximately 70% reduction in the volume of the affected nodes. In another dog with tonsillar carcinoma, we observed a partial response after several hours of low arginine achieved by selective dialysis. Both dogs died due to bleeding (at that time, there were still unresolved issues with platelet loss). We achieved remission in a third dog with osteosarcoma of the proximal humerus by infusion of lactate. This dog had three biopsies taken at 6 weeks after the treatment. All biopsies were negative and the dog had improved clinically (e.g., the pain was gone). However, several weeks later a new local lesion appeared distally to the original site, with evidence of lung metastases. It is important to note that a very low arginine level was maintained in these dogs for only about a day. The effect on the tumor given that short time was impressive indeed.

Detailed Treatment Protocol in a Canine Model: The following protocol for treating dogs with cancer was developed based on our own work with healthy experimental dogs and dogs with cancer. Dosages of known drugs were selected based on guidelines provided by the manufacturers and adjusted as needed based on physiological responses. Where only human dosages were available, we used the usual formula for conversion to dosages appropriate for dogs (multiplying by a factor of 2 to obtain a dose per kg body weight value). The treatment involves three phases: (i) a period of accommodation to the new environment and preparation for the treatment (three days); (ii) the application of the protocol (six days); and (iii) the recovery period (several days (e.g., 30 days or more)).

On Day 1, the dog is deprived of its normal food (controlled nutrition is provided as described below until the end of the treatment). It is also physically examined and blood samples are taken to obtain baseline values. If no unexpected abnormalities are found, the dog receives polyethylene glycol for whole bowel irrigation (GoLYTELY®, CoLyte® 250 ml every 10 minutes up to 3 liters, until the stool becomes watery). Antibiotics (vancomycin 5 mg/kg/day and gentamicin 2 mg/kg/day) are given for gut sterilization.

On Day 2, the dog is subjected to general anesthesia (initial sedation with midasolam, 0.1 mg/kg, i.v. and Buprenorphin, 0.007 mg/kg, i.v., induction with Propofol 2-4 mg/kg, i.v.; anesthesia maintenance with an Isofluran/O$_2$/air mixture (30% O$_2$; 1.2 minimal alveolar concentration of Isofluran)); vital signs are monitored during the anesthesia using pulsoxymetar, EKG, capnography, tidal volume and respiratory rate. A central venous catheter (standard procedure, jugular vein) and J-tube (standard surgical procedure, jejunum, 20-30 cm down from Treitz ligament) are inserted. The dog is then brought back to its cage and monitored.

On Day 3, the dog is monitored. The central venous catheter and the J-tube are flushed with saline every four hours until the treatment infusions are initiated.

On Day 4, an infusion pump system, such as Orchestra® of Fresenius for i.v. infusion and Alaska®, also of Fresenius, for parenteral feeding are set up. The setup includes programming the defined dosages for all i.v. infused drugs: insulin (0.1 U/kg/h), sodium nitroprusside (SNP) (0.06 mg/kg/h), vasopressin (0.02 U/kg/h; adjusted as needed to maintain pulse rate within a normal range), and thiosulfate (0.15 mg/kg/h). These drugs are prepared for syringe infusion. Glucose 50% (2 ml/kg/h; adjusted as needed to maintain normal levels of plasma glucose), amino acids (arginine free), and Ringer's lactate (adjusted to cover the physiological need) are also administered intravenously with peristaltic pumps of the Orchestra® system. The infusion system is started, but the line is not connected with the central venous catheter until the drugs fill the line. The Alaska® system is started to deliver an arginine-depleting enzyme composition to the small intestine. The rate of delivery, based on enzymatic activity, is above 200 units per kg per day, and up to several thousand units per kg per day, as needed to reach micromolar levels of plasma arginine.

The treatment on Days 5 to 9 is the same as that on Day 4. The dog is closely monitored throughout the treatment session.

After the ninth day, drug delivery is discontinued in a step-wise manner over 12 hours (glucose infusion is adjusted to glycemia), and the central venous catheter and J-tube are removed during a short period of anesthesia. The dog is allowed to resume normal feeding with food containing arginine and is monitored for several days after the treatment for any side effects.

An example of a process for preparing a liver extract with high arginase activity, preferably a pig liver extract, comprises the steps of: (1) providing pig liver (e.g., from a supervised slaughter house), which is preferably maintained on ice (e.g., during any required transport); (2) cutting the pig liver into small pieces and subsequently homogenizing it with a one-half to one volume of Ringer's lactate, on ice; (3) storing the homogenate on ice for several hours up to the maximum of overnight; (4) centrifuging the homogenate at 4° C. for 10 minutes at about 10000 g, until it separates into three distinct layers (a layer of cellular debris, an aqueous layer, and a fatty layer); (5) separating the aqueous layer from the other layers; (6) heating the aqueous layer at 65° C. for 10 minutes; (7) centrifuging again at 20 to 50° C. for 10 minutes, at about 10000 g; (8) separating the aqueous layer from the sediment layer; (9) concentrating the extracted aqueous layer (e.g., by ultrafiltration); adding 1000 mg of pyridoxal phosphate per liter of the liver extract; (10) filtering the liver extract on a non-pyrogenic 0.2 µm filter; (11) packaging the filtered liver extract in bags (e.g., sterile 1 liter bags); and (12) storing the packaged liver extract at 4° C. until use.

Alternatively, the steps (4) and (5) can be eliminated, i.e. the complete homogenate can be heated to 65° C. followed by one-step centrifuging.

After step (8), the aqueous layer, representing the resulting liver extract, can be concentrated by ultrafiltration or by vacuum/heat. As prepared, this extract may contain very high concentrations of glutamate and glutamine. Since both are possible precursors for production of ornithine in the intestinal lining cells, the extract can be briefly dialyzed to remove small molecules, such as amino acids. This is conveniently done in conjunction with ultrafiltration. Small molecules of known therapeutic value can then be added. Specifically, (sodium) lactate, pyridoxal phosphate and essential amino acids (e.g. leucine, isoleucine, histidine, phenylalanine, tryptophan, threonine, valine, lysine and methionine) can be added. We may refer to the filtered liver extract as HALEX (High Arginase Liver EXtract), which can be packaged in 1 liter bags and stored at 4° C. The concentrations of arginase in the HALEX can vary. For example, the HALEX can contain from 10 U/ml up to 500 U/ml of arginase. Peak activity of arginase is at a pH of 8 to 9, yet liver extract as prepared is acidic, with a pH of just over 6. It is thus advisable to increase the pH of the final preparation to about 7 to 7.5.

The table below summarizes the dosages of the substances used in the protocol.

| | Substance | Description | Initial rate | Max rate | Comment |
|---|---|---|---|---|---|
| 1 (P) | Liver extract | High arginase liver extract | 20 ml/kg/d | 35 ml/kg/d | Monitor for nausea, vomitus and diarrhea |
| 2 (S) | Insulin | Recombinant, human, APIDRA ®, SANOFI | 3 I.E./kg/d | 12 I.E./kg/d | If after 12 h plasma arginine >1 microM, escalate; if max rate not sufficient, then arginase rate is low |
| 3 (P) | Dextrose | DEXTROSE ® 50% solution HOSPIRA | 20 g/kg/d | 30 g/kg/d | Adjust to maintain normal plasma level; if max rate not enough, reduce insulin |
| 4 (S) | SNP | Sodium nitroprusside with antidote (B12a, or sodium thiosulfate) | 1.5 mg/kg/d | 3.0 mg/kg/d | If any platelet loss after 12 h, increase in steps of 0.4 |
| 5 (S) | Vasopressin | Vasopressin | 0.06 mg/kg/d | 0.12 mg/kg/d | Adjust to maintain pulse and pressure |
| 6 (P) | Amino acids | Arginine-free mix | 1 g/kg/d | 1.5 g/kg/d | Maintain plasma amino acids levels; Monitor ammonia |
| 7 (i.v.) | Diuretic | Furosemide, Lasix | 20-80 mg | | As needed |
| 8 (p.o. i.v.) | Antibiotics | Non-absorbable (e.g. vancomycin + gentamicin) plus systemic | | | Gut sterilization + prophylactic |

(S) denotes preferable use of a syringe pump; (P) of a peristaltic pump.

Metoclopramide can be administered to treat vomiting.

Inclusion/Exclusion and Post-inclusion Removal Criteria: Where healthy dogs are studied, they will be selected according to the following criteria: (1) of known origin and properly identified; (2) previously untreated with any form of conventional or experimental drug treatment, including radiation or chemotherapy, that may have compromised normal organ and bone marrow function; (3) at least 2 years old but less than 15 years old; (4) a life expectancy greater than twelve months; and (5) laboratory and physical findings as defined below:

| | |
|---|---|
| leukocytes | ≥6,000/µl |
| absolute neutrophil count | ≥4,000/µl |
| platelets | ≥150,000/µl |
| total bilirubin | ≤3.4 µmol/l |
| albumin | ≥25 g/l |
| creatinine | ≤100 µmol/l |
| Temperature | 38.3-39.2° C. |
| Pulse rate (small breed) | 90-160 |
| Pulse rate (middle breed) | 80-130 |
| Exhalation | 10-30 |

Both male and female dogs of all breeds are eligible for these studies.

Dogs will be excluded where they have a history of allergic reactions attributed to compounds of chemical or biologic composition similar to agents used in study, a history of diabetes, uncontrolled inter-current illness (including, but not limited to, ongoing or active infection, symptomatic congestive heart failure, cardiac arrhythmia or a temperament that would limit compliance with study requirements) or are pregnant or lactating.

Feeding: Dogs receive food during the accommodation and follow-up phases but are deprived of normal food during the protocol phase, during which they are fed with HALEX or another composition as described herein.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a patient who has an arginine-dependent cancer, the method comprising:
   (a) identifying a patient who has an arginine-dependent cancer of the liver, breast, bone, lung, pancreas, skin, reproductive system, brain, blood, or soft connective tissues; and
   (b) administering an arginine-depleting enzyme or a biologically active variant thereof directly to the lumen of the patient's small intestine, thereby systemically depleting arginine and treating the arginine-dependent cancer.

2. The method of claim 1, wherein the arginine-depleting enzyme is an arginase, an arginine decarboxylase, an arginine deiminase, an arginine kinase, an arginine 2-monooxigenase, or a glycine amidinotransferase.

3. The method of claim 2, wherein the arginine-depleting enzyme is an arginase.

4. The method of claim 3, wherein the arginase is an arginase Type 1.

5. The method of claim 1, wherein the arginine-depleting enzyme is administered with or within a liver extract, within intact yeast cells, within a lysate of yeast cells, within bacterial cells, or within a lysate of bacterial cells.

6. The method of claim 5, wherein the liver extract is in crude form or partially purified and/or concentrated by the removal of liquid or sterilized; the yeast cells are a strain of *Saccharomyces cerevisiae;* or the bacterial cells are *Bacillus caldovelox.*

7. The method of claim 1, further comprising administering one more of the following: an essential co-factor of the arginine-depleting enzyme; an ornithine depleting enzyme; pyridoxal phosphate; lactate; Gly-Gly-PALO; gabaculine; insulin; glucose; dextrose; fructose; an antibiotic; a nitric oxide donor; a pressor peptide; and prostacycline or an analog thereof.

8. The method of claim 1, further comprising administering an amino acid mixture lacking arginine, ornithine, and citrulline but containing at least: leucine, isoleucine, histidine, phenylalanine, tryptophan, threonine, valine, lysine and methionine.

9. The method of claim 1, further comprising administering physiological electrolytes.

10. The method of claim 1, wherein the arginine-depleting enzyme is an arginine-depleting enzyme naturally expressed by an animal cell, a bacterial cell, or a yeast cell.

11. The method of claim 10, wherein the animal cell is a human cell.

12. The method of claim 1, wherein the arginine-depleting enzyme is administered at a rate equal to or higher than 200 units per kilogram per day.

13. The method of claim 1, wherein the arginine-depleting enzyme or the biologically active variant thereof is administered directly to the lumen of the patient's small intestine through a feeding tube.

14. The method of claim 13, wherein the feeding tube is a nasointestinal feeding tube.

15. The method of claim 13, wherein the feeding tube is inserted through a jejunostomy, esophagostomy, or gastrostomy.

* * * * *